US005765682A

United States Patent [19]
Bley et al.

[11] Patent Number: 5,765,682
[45] Date of Patent: Jun. 16, 1998

[54] RESTRICTIVE PACKAGE FOR EXPANDABLE OR SHAPE MEMORY MEDICAL DEVICES AND METHOD OF PREVENTING PREMATURE CHANGE OF SAME

[75] Inventors: Bob Bley, Menlo Park; Kevin Van Bladel, Mountain View, both of Calif.

[73] Assignee: Menlo Care, Inc., Menlo Park, Calif.

[21] Appl. No.: 669,579

[22] Filed: Jun. 24, 1996

Related U.S. Application Data

[63] Continuation of Ser. No. 322,608, Oct. 13, 1994, abandoned.

[51] Int. Cl.$^6$ .................................................... B65D 83/10
[52] U.S. Cl. ........................... 206/363; 206/438; 206/364
[58] Field of Search ........................ 206/363, 364, 206/365, 438, 440, 497, 542.8, 528, 529, 571; 606/108; 604/171, 264, 281, 358; 383/207, 208, 209; 609/11, 12, 904

[56] References Cited

U.S. PATENT DOCUMENTS

| | | | |
|---|---|---|---|
| Re. 29,343 | 8/1977 | Amplatz | 53/21 FC |
| Re. 31,855 | 3/1985 | Osborne | 604/161 |
| 3,259,235 | 7/1966 | Sowle | 206/497 |
| 3,411,620 | 11/1968 | Steinbock | 206/63.2 |
| 3,473,646 | 10/1969 | Burke | 206/47 |
| 3,570,485 | 3/1971 | Reilly | 128/214.4 |
| 3,612,038 | 10/1971 | Halligan | 128/2.05 R |
| 3,677,243 | 7/1972 | Nerz | 128/214.4 |
| 3,750,875 | 8/1973 | Juster | 206/364 |
| 3,856,143 | 12/1974 | Simon et al. | 206/438 |
| 3,934,721 | 1/1976 | Juster et al. | 206/364 |
| 4,306,562 | 12/1981 | Osborne | 128/348 |
| 4,411,655 | 10/1983 | Schreck | 604/165 |
| 4,412,832 | 11/1983 | Kling et al. | 604/164 |
| 4,418,514 | 12/1983 | Spann | 206/524.8 |
| 4,424,305 | 1/1984 | Gould et al. | 525/127 |
| 4,480,642 | 11/1984 | Stoy et al. | 128/341 |
| 4,533,356 | 8/1985 | Bengmark et al. | 604/358 |
| 4,557,385 | 12/1985 | Robinson | 383/208 X |
| 4,610,357 | 9/1986 | Nakamura | 383/207 X |
| 4,648,867 | 3/1987 | Conner et al. | 604/14 |
| 4,676,773 | 6/1987 | Sheldon | 604/16 |
| 4,738,667 | 4/1988 | Galloway | 604/281 |
| 4,772,275 | 9/1988 | Erlich | 206/364 X |
| 4,779,727 | 10/1988 | Taterka et al. | 206/364 |
| 4,798,876 | 1/1989 | Gould et al. | 525/457 |
| 4,811,847 | 3/1989 | Reif et al. | 206/571 |
| 4,877,132 | 10/1989 | Makris et al. | 206/364 |
| 4,878,903 | 11/1989 | Mueller | 206/364 |
| 4,883,699 | 11/1989 | Aniuk et al. | 428/36.9 |
| 4,911,691 | 3/1990 | Aniuk et al. | 604/164 |
| 4,923,061 | 5/1990 | Trombley, III | 206/364 |
| 4,925,448 | 5/1990 | Bazaral | 604/171 |
| 4,950,257 | 8/1990 | Hibbs et al. | 604/265 |
| 4,952,359 | 8/1990 | Wells | 264/139 |
| 4,994,047 | 2/1991 | Walker et al. | 604/264 |
| 5,048,684 | 9/1991 | Scott | 206/364 |
| 5,067,612 | 11/1991 | Tsuchiyou et al. | 206/467 |
| 5,071,407 | 12/1991 | Termin et al. | 604/104 |

(List continued on next page.)

OTHER PUBLICATIONS

"About O.B. Tampons" Informational Article, Date Unknown See Fig. 1.

"Development of Polymeric Shape Memory Material", Yoshiki Shirai & Shun–ichi Hayashi, Nagoya Research & Development Center, Technical Headquarters, MTB 184, Dec. 1988, pp. 1–5.

*Primary Examiner*—David T. Fidei
*Attorney, Agent, or Firm*—Blakely, Sokoloff, Taylor & Zafman

[57] ABSTRACT

A package for a medical device made of an expandable or shape memory material is disclosed. The package is a sheath which surrounds and contains the medical device, and is of sufficient strength that upon exposure to conditions which would cause the medical device to expand or change its shape it is restrained from such shape change or expansion. The package has a tear-away or peel-away feature which provides easy access to the medical device when needed.

27 Claims, 3 Drawing Sheets

U.S. PATENT DOCUMENTS

| | | | |
|---|---|---|---|
| 5,078,720 | 1/1992 | Burton et al. | 606/108 |
| 5,105,942 | 4/1992 | van Venn et al. | 206/364 |
| 5,131,537 | 7/1992 | Gonzales | 206/364 |
| 5,153,971 | 10/1992 | Van Iten | 604/358 |
| 5,178,611 | 1/1993 | Rosenberg . | |
| 5,221,263 | 6/1993 | Sinko et al. | 604/161 |
| 5,282,789 | 2/1994 | Lundy | 604/55 |
| 5,332,092 | 7/1994 | Fischer et al. | 206/365 |
| 5,409,469 | 4/1995 | Schaerf | 604/282 |
| 5,445,646 | 8/1995 | Eutenauer et al. | 606/198 |

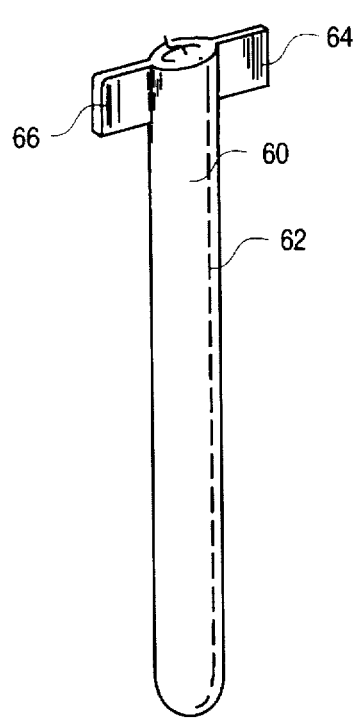
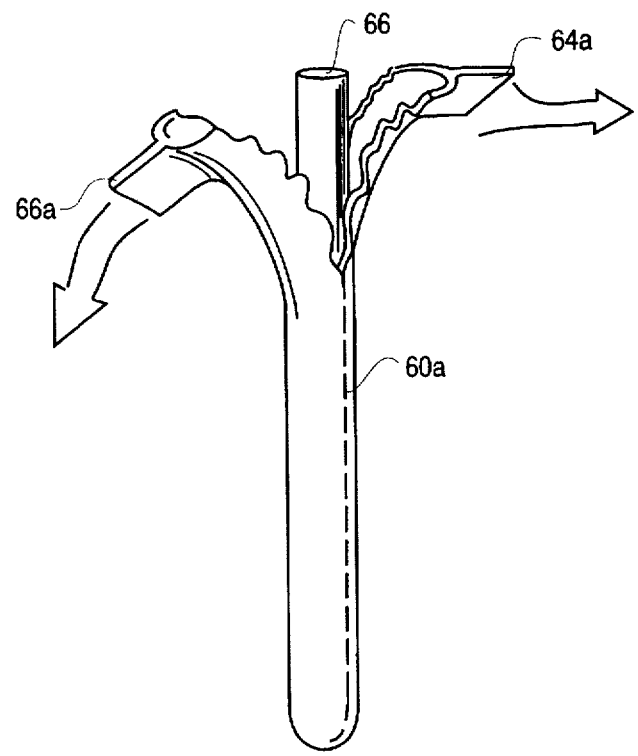
FIG. 10A  FIG. 10B
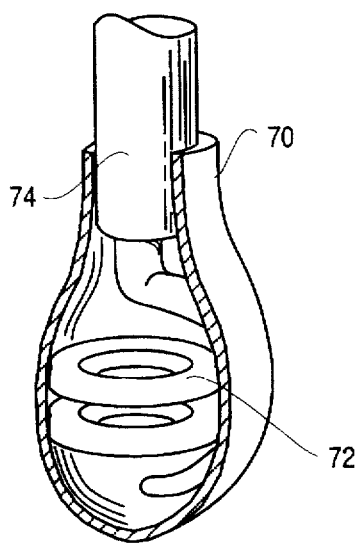
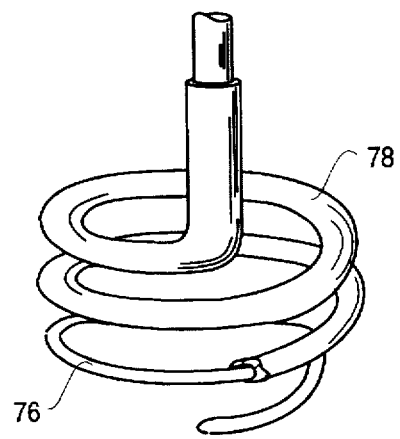
FIG. 11  FIG. 12

RESTRICTIVE PACKAGE FOR EXPANDABLE OR SHAPE MEMORY MEDICAL DEVICES AND METHOD OF PREVENTING PREMATURE CHANGE OF SAME

This is a continuation of application Ser. No. 08/322,608, filed Oct. 13, 1994, now abandoned.

BACKGROUND OF THE INVENTION

1. Field of the Invention

This invention relates to medical devices, such as stents, catheters and cannulas formed into a first shape and size, which devices, when heated or exposed to liquids, conform to a second or shape memory, and more particularly, to packaging for maintaining such devices in their first shape and size. More specifically, the present invention is directed to a restrictive tear-away packaging which will prevent the premature expansion or re-conformation of medical devices with a shape memory, and provide easy access to the medical device when needed.

2. Art Background

Catheters are well-known in the art for fluid injection into, and removal from, human or other animal bodies. They are placed partially within the body and anchored there during use. Stents, another type of medical tube, are used to communicate fluid within the body from one location to another. Other tubes are used for various medical purposes, such as feeding tubes, endotracheal tubes and naso-gastric tubes, for example. It is desirable that many of these medical tubes maintain different shapes, sizes and hardnesses, namely, a first shape, size and hardness advantageous for insertion into the body, and a second shape, size and hardness most advantageous for the conditions where the tube is inserted and remains in the body for an extended period of time. More specifically, it is desirable that during insertion the tube should be relatively stiff, as small as possible, and generally straight. The tube is preferably stiff so that it can be pushed from its distal end into the body (although not so stiff that it can't negotiate turns). The tube is preferably small so that it can easily fit into a small hole, orifice or cavity with minimal trauma or discomfort to the patient. The tube is preferably straight because it is difficult to install a non-straight tube into a generally straight vessel or the like. After insertion into the body, it is often desirable for the tube to take on a second configuration, shape and hardness. A soft tube is more comfortable and less irritating than a hard one, and a large diameter tube can carry more fluid in a limited period of time than a small diameter tube. Regarding the shape, tubes are sometimes made with a shape memory which advantageously fits in the portion of the body for which the tube is particularly used. For example, some tubes designed for endo-tracheal use may contain a natural curve to accommodate the pathway up and through the nasal passage, and down the trachea. However, it is not generally desirable for such tubes to take on that second configuration until after the tube is inserted in the body. As another example, there are medical devices which are designed for implantation in the body which have shapes other than tube-like shapes, or which have irregular shapes. Such devices include cervical dilators, vaso-occluders, devices, such as stents with pigtail-shaped anchoring systems, and binary stents with barb-shaped anchoring systems.

A commercially desirable medical tube device, such as a stent, is typically expandable in diameter only, because conservation of the original length is important for the tube to function properly if it is entirely within the body, such as with a stent. One way of achieving the unidirectional (radial only) change in dimensions is to impart a stress on the linear direction that is equal to the stress of expansion of the material upon hydration. A polymer made of a hydrogel and an elastomer can be heated above the Tg or melting point of the hydrogel, but to a temperature less than the shape forming temperature of the elastomer. The tube is then stretched to the length it will achieve when hydrated, and then it is cooled to a temperature below the Tg or melting point of the hydrogel. The hydrogel then holds the elastomer in the stretched configuration until hydration of the hydrogel, at which time the hydrogel weakens, and loses its ability to retain the elastomer in its stretched configuration, but the swelling of the hydrogel causes the stent to maintain its constant length. Another shape memory system utilizes Nitinol, a shape memory metal.

The technology for making such shape memory devices are described in a number of prior art references, such as Walker, et al., U.S. Pat. No. 4,994,047 which discloses a polymeric cannula structure which enlarges and softens at body temperature in the presence of water and Shreck, U.S. Pat. No. 4,411,655, which utilizes a helically wound shape memory alloy formed into a catheter.

Other materials which can be made into expandable medical tubes include polyacrylonitrile (hydrolyzed) (see U.S. Pat. No. 4,480,642); polyurethane diacrylate (see U.S. Pat. No. 4,424,305); hydrophilic polyether polyurethane and hydrophobic polyester polyurethane (see U.S. Pat. No. 4,798,876), and hydrogels (PEO-polyethylene oxide, PVP-polyvinylpyrrolidone, PVA-polyvinyl alcohol, and pHEMA-polyhydroxyethylmethacrylate).

Medical devices of the type described above are typically packaged for the purpose of maintaining sterility, and to protect the device from damage, twisting, kinking or the like until it is used. Many different types of packaging have been employed. U.S. Pat. No. 5,105,942 discloses a blister pack made of a flat lower sheet of plastic, cardboard, or plastic coated cardboard, and an upper sheet made of plastic, and having a pressed out portion that conforms generally to the shape of the catheter, the lower and upper sheets being attached together at their periphery, generally by heat sealing. This patent discloses that the blister pack protects the catheter when it is heated during sterilization by maintaining the curved portion of the catheter in its curved configuration.

Burke, U.S. Pat. No. 3,473,646 discloses a blister pack for a syringe assembly which includes medication pre-loaded into the syringe, and the blister pack is formed with a recess to prevent the syringe from moving until it is removed from the package.

Halligan, U.S. Pat. No. 3,612,038 allows the physician or technician to preform a straight catheter shortly before use by including a wire for holding the catheter in the desired shape while heating the catheter to a critical temperature and then allowing it to cool. The package surrounding the catheter is a loose envelope.

Makris et al., U.S. Pat. No. 4,877,132 discloses a generally cylindrical tube with several internal flanges for retaining a syringe in a filled or empty configuration.

Gonzales, U.S. Pat. No. 5,131,537 discloses packaging medical catheters, particular those with a curved tip portion, and including a tray with a preformed curvature which conforms to the shape of the catheter, and a flat sheet with flexible cutouts which retain the straight portion of the catheter.

Trombley, III, in U.S. Pat. No. 4,923,061 describes a catheter curve retention device in the form of a package with a shaped pocket to retain the curve of the catheter in a proper form, and a pair of plastic sheets which are disposed below and above the catheter to maintain it sterile and protect it. The sheets can be torn apart to provide access to the catheter.

U.S. Pat. No. 5,048,684 discloses a package for a containing a plurality of syringes, the package being formed of two mating sheets with a preformed recess in each to conform to the shape of the plurality of syringes. The sheets are each thermoformed to contain the recesses.

Other catheter and other medical tube packages are disclosed in U.S. Pat. Nos. 4,811,847; 4,779,727; 3,934,721; 3,411,620; 4,925,448; and Re. 29,343.

However, none of these prior art packages appear to be capable of preventing a shape memory medical device from regaining is shape memory configuration if conditions which would cause the shape to change, such as high temperatures or humidity, are encountered.

Galloway, U.S. Pat. No. 4,738,667 discloses a catheter assembly in which the catheter has a pigtail or other three dimensional arrangement at one end, and a lose sheath is disposed over the pigtail to make it straight so that the catheter can be inserted into the body. After insertion, the sheath is slid off the pigtail portion of the catheter, allowing the pigtail to regain its shape, which holds the catheter in place inside a cavity.

In several prior art medical devices, peel-away or tear-away sheaths, sometimes referred to as introducer sheaths, are utilized to implant a catheter in a vein. The sheath is used to puncture the skin and tissue and get into the blood vessel. The catheter is then introduced into the blood vessel through the middle of the sheath. The sheath is then withdrawn by sliding it over the catheter and out of the blood vessel, and once clear of the patient, it is split along its longitude to remove it from the catheter. Such devices are shown in U.S. Pat. Nos. 5,221,263; 4,412,832; Re. 31,855; 3,570,485; 4,952,359; and 3,677,243.

However, the peel-away concept has not heretofore been applied to packages for shape memory medical devices and the like.

SUMMARY OF THE INVENTION

The present invention is directed to a package for a medical device made of an expandable or shape memory material, the package comprises a sheath which surrounds and contains the medical device, and has an appropriate size relative to the medical device and is of sufficient strength that upon exposure to conditions which would cause the medical device to expand or change its shape it is restrained from such shape change or expansion. The package is preferably tightly wrapped around the medical device, or there may be some clearance. The package in its presently preferred embodiment has a tear-away or peel-away feature which provides easy access to the medical device when needed. However, the tear-away or peel-away feature is sufficiently strong that it prevents a change in the size or shape of the medical device upon exposure to the elevated temperature required for such change. The tear-away feature can be, for example, a perforated or otherwise weakened section of the sheath along its length, an embedded string, a strip of material of a different composition than the remainder of the sheath, or other tear-away feature systems that are known in the art. A peel-away feature can be, for example, an adhesively bound strip of material disposed over a hole along the length of the sheath. The package of the present invention can surround an entire medical device or only a portion thereof.

As used herein, the term medical device shall include a device used in a medical procedure in which expansion or other shape change occurs upon exposure to a predetermined condition, for the purpose of positioning or expansion of the device. Examples of such medical devices include stents, catheters and feeding and breathing tubes, and more specifically can include, but are not limited to, ureteral stents, biliary stents, nephrostomy catheters, feeding tubes, endotracheal tubes, intermittent catheters, Hickman or Foley catheters, cervical dilators, fallopian tube occluders, cervical dilators and the like.

BRIEF DESCRIPTION OF THE DRAWINGS

FIG. 10A is an illustration of a perspective view of an alternative embodiment of the present invention illustrating a tear apart package covering a medical device in a tube-like shape.

FIG. 10B is a perspective view of the packaged device of FIG. 10a wherein the package is partially removed.

FIG. 11 is a sectional view of an alternative embodiment of the present invention wherein a package retains a pig-tail shaped anchor system in a compressed configuration.

FIG. 12 is a perspective partially cutaway view of an alternative embodiment of the present invention wherein a pigtail is covered with the package system of the present invention.

DETAILED DESCRIPTION OF THE INVENTION

Figure 6:
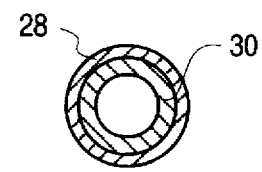
FIG. 6 is an illustration of the expansion of an expandable medical device as is known in the prior art.

Expandable medical devices are known in the art. FIG. 6 shows that a collapsed medical tube 10 has a smaller outer diameter than the expanded medical tube 12. When the collapsed tube is exposed to a predetermined condition depending upon the material from which it is made, such as, for example, a liquid, or an elevated temperature of about 98.6° F. (37° C.), like body temperature, the tube changes its conformation. The present invention is directed to a package which prevents that change in conformation. The present invention also prevents a medical device from re-conforming to a shape memory upon exposure to such predetermined conditions.

Figure 1:
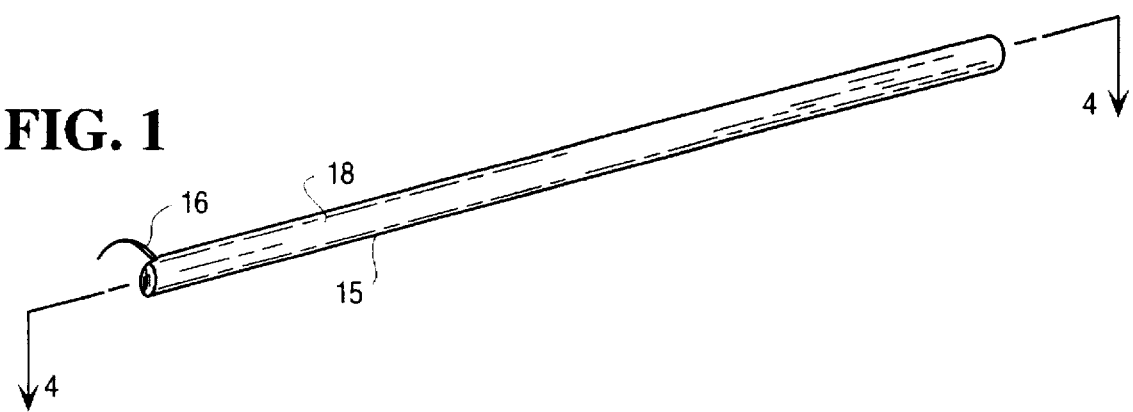
FIG. 1 is a perspective view of a medical device encapsulated in a sheath in accordance with the present invention.
Figure 2:
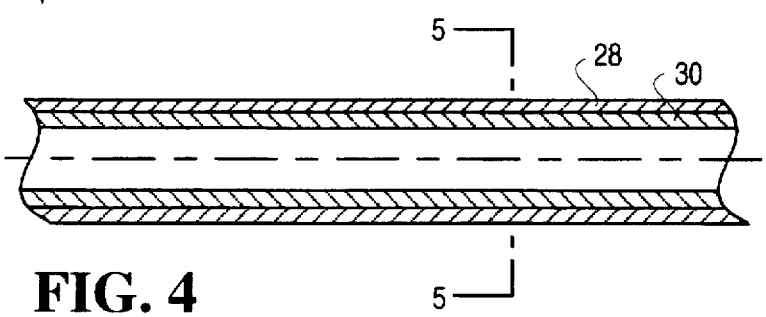
FIG. 2 is a perspective view of a medical device in a sheath in a partially opened conformation.

As shown in FIG. 1, one embodiment of the present invention comprises a sheath 15. The sheath 15 has a string 18 embedded therein along its length and the string 18 has a loose end 16 to facilitate the handling thereof. As shown in FIG. 2 in another embodiment of the present invention, when the end 17a is pulled upward, it ruptures the wall 19 of the sheath 21 exposing the medical tube 20 disposed therein in its collapsed condition. Once the tube is removed from the sheath it can be used for its intended medical purpose and then permitted to expand or otherwise change shape.

The sheath is made of a strong plastic material, such as polyvinyl chloride (PVC), polyesters, such as PET, polypropylene, polyamide, aliphatic polyesters, high density polyethylene, ethylene copolymers such as ethylene vinyl acetate copolymer and ethylene ethoxy acrylate copolymer, polyurethane, acrylonitrile butadiene styrene, ABS, nylon, such as Nylon 12, and fluoropolymers such as Teflon® (DuPont), FEP, PFA, polytetrafluoroethylene (PTFE), TFE, and Tefzel, and other plastics of sufficient strength to resist the expansion forces of the medical tube disposed therein if the medical tube is exposed to temperature or other predetermined conditions which would otherwise permit it to expand. Such predetermined conditions may be temperature as described above, or humidity. For purposes of clarity, the present invention will primarily be described with reference to shape memory devices activated by temperature.

One particularly preferred material is Aquavene® (Menlo Care) as disclosed in U.S. Pat. Nos. 4,883,699 and 4,911,691.

The sheath has sufficient strength to withstand the expansion forces of the medical device being packaged. The strength may be temperature dependent, in that, if the medical device is made of a is shape memory polymer which is stable at room temperature, the required strength at room temperature is minimal. However, the strength must be sufficient at elevated temperatures to resist the shape memory polymer's shape change. The sheath can be vacuum formed, extruded, heat shrinkable, molded or otherwise formed shape with the appropriate inner shape and dimensions for its intended purpose.

Preferably the sheath material has a heat deflection temperature above around 65° C. at 264 psi, which is the temperature at which a material subjected to a 264 psi load will deflect.

The wall thickness should preferably be as thin as possible as long as the requisite strength is present. Preferably the wall thickness is in the range of 0.003 to 0.020 inches (0.0762 mm to 0.508 mm).

In an alternative embodiment the sheath may be made of a dissolvable material, such as a hydrophilic material such as polyethethylene oxide (PEO), polyvinyl pyrrolidone (PVP) or polyvinyl alcohol (PVA). The sheath material may be extruded onto the medical device, or the medical device may be dip-coated, spray-coated or otherwise covered with the sheath, and allowed to dry on the medical device.

In an alternative form of application of the sheath, a sheath of a first predetermined length and internal diameter is stretched to a longer length, which necessarily requires that the internal diameter be reduced. Thus, if the sheath is applied over a medical device and then stretched to a smaller diameter, it can securely be formed to an appropriate shape and size to retain the medical device in its desired shape until the sheath is removed.

In another alternative method of applying the sheath to a medical device, a medical device of a first predetermined length and external dimension is stretched to a longer length, which necessarily requires that the external dimension is reduced. Thus, the sheath can be applied over a medical device and then, the medical device is released allowing it to enlarge up to the internal diameter of the sheath. If the medical device is heated before it is stretched to facilitate the stretching, and allowed to cool and conform to a smaller external dimension than when it is unstretched, it can securely be held in to its appropriate size in the sheath even if it is exposed to higher temperatures which would otherwise permit a reconformation to the original size.

Figure 3:
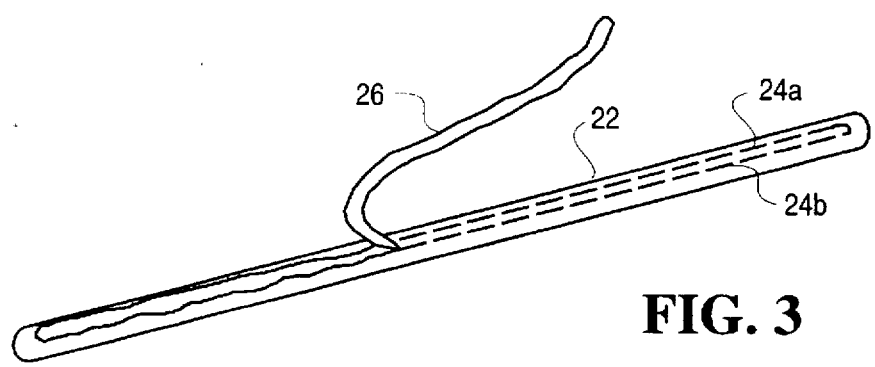
FIG. 3 is a perspective view of a sheath of the present invention with an alternative embodiment opening system comprising a perforated strip.

As shown in FIG. 3, various alternative opening systems may be employed. In FIG. 3, the sheath 22 has a pair of perforated lines or scribe lines 24a and 24b disposed in a line along its length, and a flap 26 can be pulled upward away from the sheath 22 to expose the inside thereof. Alternatively, the wall may be partially sliced or only partly formed, or otherwise weakened.

Figures 4, 5:
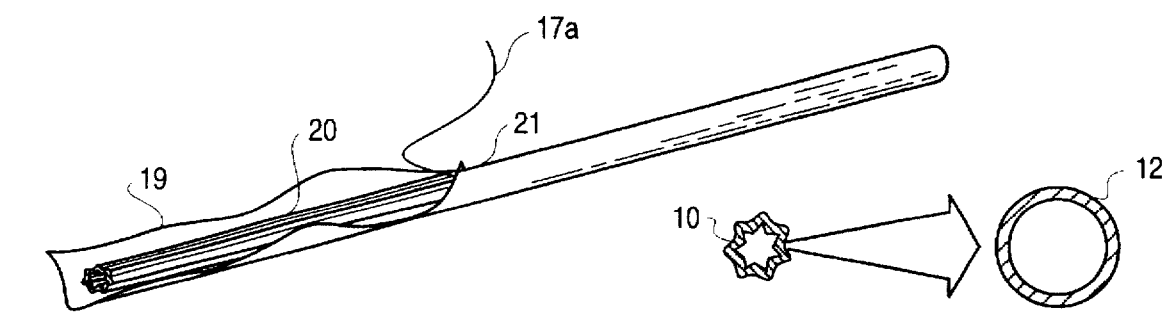
FIG. 4 is an enlarged side sectional view of the invention shown in FIG. 1 taken through lines 4—4 of FIG. 1.
FIG. 5 is an enlarged end sectional view of the invention shown in FIG. 1 taken through lines 5—5 of FIG. 4.

As shown in FIGS. 4 and 5, the sheath 28 tightly constrains the medical tube 30 therewithin to prevent it from expanding.

Figure 7A:
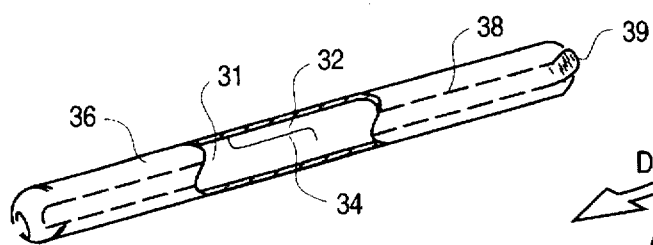
FIG. 7A is an illustration of a perspective partially cutaway view of an alternative embodiment of the present invention wherein a medical device with an anchoring system of the type used with a biliary stent is shown in its packaged configuration.
Figure 7B:
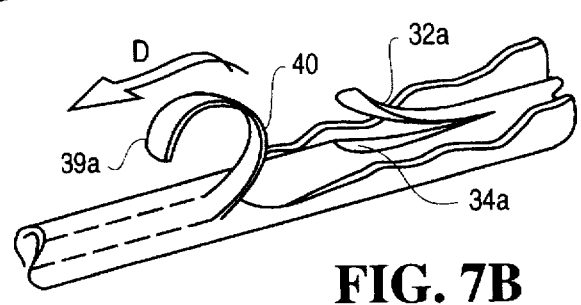
FIG. 7B is an illustration of a perspective view of the packaged device of FIG. 7A wherein the package is partially removed.

FIGS. 7A and 7B illustrate another embodiment of the present invention. FIG. 7A shows an embodiment of the present invention in which the medical device is not a simple tube, but rather, the medical device 31 has a barb or anchor 32 that is retained against the body 34 of the device until released from the sheath 36. FIG. 7A is shown in partially cutaway view to show the medical device 31, it being understood that in this embodiment the sheath 36 would generally completely enclose the medical device 31. A pair of scribe lines 38 are provided to permit removal of the sheath 36 from the medical device 31. A tab 39 permits easy removal of the sheath 36. As shown in FIG. 7B, when the tab 39a is pulled in direction shown by the arrow labeled D, a strip 40 is formed. Also, the barb 32a springs upward from the body 34a when the device 31 is exposed to conditions, such as elevated temperature or humidity, which cause a change in shape.

Figure 7C:
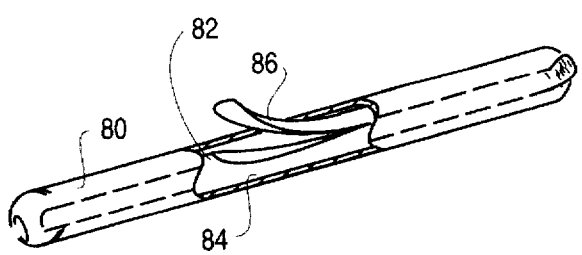
FIG. 7C is an illustration of a perspective view of an alternative embodiment of the present invention wherein a medical device with an anchoring system of the type used with a biliary stent is shown in its packaged configuration.

As shown in FIG. 7C, a sheath 80 is provided to contain and retain a medical device 82. A window 84 is provided in the sheath 80 to permit an irregularly shaped portion 86 to stick out. In this way, irregularly shaped members do not necessarily have to be covered with a sheath, such as in cases where such covering is not desirable, or it is difficult to provide a sheath which covers such member due to the irregular shape.

Figure 8B:
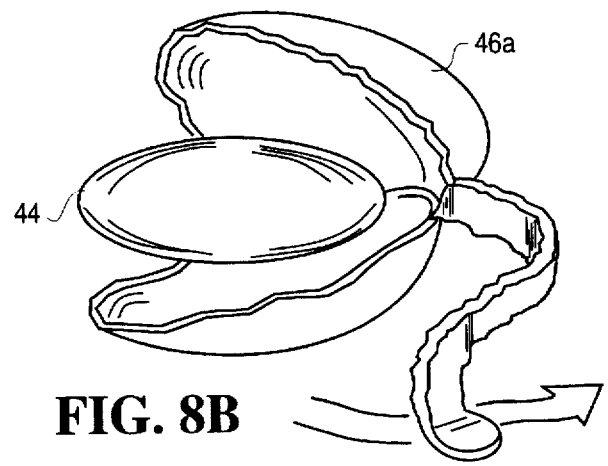
FIG. 8B is a perspective view of the packaged device of FIG. 8A wherein the package is partially removed.
Figure 8A:
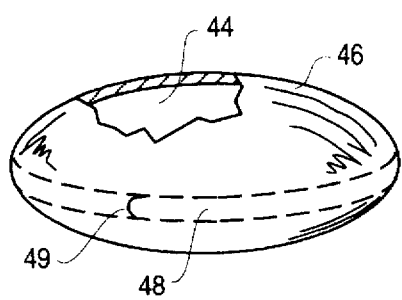
FIG. 8A is an illustration of a perspective partially cutaway view of an alternative embodiment of the present invention wherein a medical device of a non-tubular configuration is shown in its packaged configuration.

As shown in FIGS. 8A and 8B, the medical device may be of any shape, and is not necessarily tube-shaped. As shown in FIG. 8A, which is a partially cutaway view of the present invention a medical device 44 which is made of an expandable, or shape memory material is enclosed in a package or sheath 46 having a scribed section 48 for easy opening of the package 46. As shown in FIG. 8B, when the pull tab 49 is pulled, it opens the package 46a allowing access and removal of the medical device 44. The package 46 may either be tightly wrapped around the medical device 44, or may be loosely wrapped around the medical device with some clearance, provided that the clearance does not permit expansion or shape change of the medical device beyond a desired amount.

Figure 9:
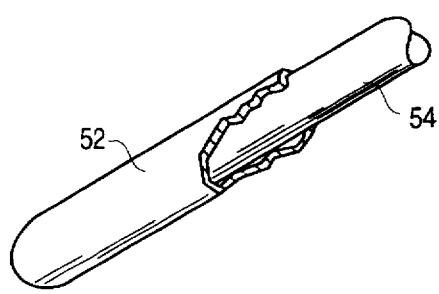
FIG. 9 is a perspective partially cutaway view of a packaged device of an alternative configuration wherein the package partially covers the medical device.

As shown in FIG. 9, which is a cutaway perspective view of an alternative embodiment of the present invention, the sheath 52 covers over only a portion of the medical device 54, depicted in FIG. 9 as a tube. This embodiment may be utilized when only a portion of the medical device is made of shape memory material, or when the retention of the shape is only important for a portion of the medical device.

As shown in FIGS. 10A and 10B, the present invention can be made with a tear away feature, which is the presently preferred embodiment. This tearaway feature is known in the art for other applications. As shown in FIG. 10A, the present invention comprises a medical device encased in a sheath 60 with a scribe line 62 to facilitate tearing or opening of the sheath. The sheath comprises a pair of tabs 64 and 66 which may be pulled apart as shown in FIG. 10B as 64a and 66a so that the medical device 66 is exposed and can be removed from the sheath 60a.

In yet another embodiment of the present invention, shown in FIG. 11, the sheath 70 surrounds a pigtail 72 of a stent 74 or similar tube to keep it in a tightly wound configuration.

In yet another embodiment, shown in FIG. 12, and irregular shape, such as a pigtail 76 or any other shape can be contained in a sheath 78 directly.

It will be obvious to a person of ordinary skill in the art that numerous modifications and changes can be made to the above apparatus in order to accomplish the same function without departing from the spirit and scope of the present invention.

What is claimed is:

1. An assembly including a medical device and a package therefor, wherein said medical device is one of a catheter and a stent device, the medical device being shaped to have a continuous passage therethrough and made of a shape memory material or an expanding material which changes shape or expands, respectively, when exposed to a predetermined condition, said predetermined condition comprising exposure to an elevated temperature or a liquid, wherein said package comprises a sheath disposed around said medical device, said sheath comprising material that prevents expansion or a change in shape of said medical device upon exposure of said medical device and sheath assembly to said predetermined condition, wherein said sheath is removed before said medical device is placed in a body cavity.

2. The assembly of claim 1 wherein said sheath further comprises a line of weakened material disposed along its length whereby upon applying a force to said line of weakened material, said sheath is opened to expose said medical device for access thereto.

3. The assembly of claim 1 wherein said sheath further comprises a string embedded therein along the length of said sheath, whereby pulling said string causes a rupture in the sheath to expose said medical device for access thereto.

4. The assembly of claim 1 wherein said sheath further comprises a hole along its length with a patch covering said hole removably adhered thereto.

5. The assembly of claim 1 wherein said sheath is tightly constricting said medical device.

6. The assembly of claim 1 wherein said sheath surrounds said medical device with some clearance.

7. The assembly of claim 1 wherein said medical device comprises an irregularly shaped portion, and said sheath further comprises a window aligned with said irregularly shaped portion, wherebe said irregularly shaped portion extends through said window.

8. The assembly of claim 1 wherein said sheath is made of a material which has a deflection temperature of above about 65° C. at 264 pounds per square inch.

9. The assembly of claim 1 wherein said sheath is made of a material selected from the group consisting of polyvinyl chloride, polyesters, polypropylene, polyamide, aliphatic polyesters, high density polyethylene, ethylene copolymers, polyurethane, acrylonitrile butadiene styrene, ABS, nylon, and fluoropolymers.

10. The assembly of claim 1 wherein said material is a dissolvable material.

11. The assembly of claim 10 wherein said dissolvable material is a hydrophilic material selected from the group consisting of polyethethylene oxide, polyvinyl pyrrolidone and polyvinyl alcohol.

12. A package for a metallic medical device, said medical device being made of a shape memory material or an expanding material which changes shape or expands respectively when exposed to a predetermined condition, said predetermined condition comprising exposure to an elevated temperature, said package comprising a sheath enclosing the medical device, said sheath comprising a material that prevents expansion or a change in shape of the medical device upon exposure of said medical device and sheath assembly to said predetermined condition, said sheath further comprising a tear-away means of opening for providing access to said medical device disposed therein, wherein said sheath is removed before said medical device is placed in a body cavity.

13. The package of claim 12 wherein said sheath further comprises a line of weakened material disposed along its length whereby upon applying a force to said line of weakened material, said sheath is opened to expose said medical device for access thereto.

14. The package of claim 12 wherein said sheath further comprises a string embedded therein along the length of said sheath, whereby pulling said string causes a rupture in the sheath to expose said medical device for access thereto.

15. The package of claim 12 wherein said sheath further comprises a hole along its length with a patch covering said hole removably adhered thereto.

16. The package of claim 12 wherein said sheath is tightly constricting said medical device.

17. The package of claim 12 wherein said sheath is made of a material which has a deflection temperature of above about 65° C. at 264 pounds per square inch.

18. An assembly including a medical device and a package therefor, wherein said medical device is a communicative device and is made of a shape memory material or an expanding material which changes shape or expands respectively when exposed to a predetermined condition, wherein said medical device has a first configuration having a first length and a first dimension and a second configuration having a second length and a second dimension, said second length being longer than said first length, said second diameter, being smaller than said first diameter, wherein said package comprises a sheath disposed around said medical device, said sheath comprising a material that prevents expansion or a change in shape of said medical device upon exposure of said medical device and sheath assembly to said predetermined condition, wherein said sheath holds said medical device in said second configuration, and wherein said sheath is removed before said medical device is placed in a body cavity.

19. The assembly of claim 18 wherein said sheath further comprises a line of weakened material disposed along its length whereby upon applying a force to said line of weakened material, said sheath is opened to expose said medical device for access thereto.

20. The assembly of claim 18 wherein said sheath is tightly constricting said medical device.

21. The assembly of claim 18 wherein said sheath surrounds said medical device with some clearance.

22. The assembly of claim 18 wherein said sheath is made of a material which has a deflection temperature of above about 65° C. at 264 pounds per square inch.

23. The assembly of claim 18 wherein said sheath is made of a material selected from the group consisting of polyvinyl chloride, polyesters, polypropylene, polyamide, aliphatic polyesters, high density polyethylene, ethylene copolymers, polyurethane, acrylonitrile butadiene styrene, ABS, nylon, and fluoropolymers.

24. A package for a medical device, said medical device is a communicative device being made of a shape memory material or an expanding material which changes shape or expands, respectively, when exposed to a predetermined condition, wherein said medical device has a first configuration having a first length and a first dimension and a second configuration having a second length and a second dimension, said second length being longer than said first length, said second dimension being smaller than said first dimension, said package comprising a sheath enclosing said medical device, said sheath comprising a material that prevents expansion or a change in shape of said medical device upon exposure of said medical device and sheath assembly to said predetermined condition, said sheath further comprising a tear-away means of opening for providing access to said medical device disposed therein, wherein said sheath holds said medical device in said second configuration and wherein said sheath is removed before said medical device is placed in a body cavity.

25. The package of claim 24 wherein said sheath further comprises a line of weakened material disposed along its length whereby upon applying a force to said line of weakened material, said sheath is opened to expose said medical device for access thereto.

26. The package of claim 24 wherein said sheath is tightly constricting said medical device.

27. The package of claim 24 wherein said sheath is made of a material which has a deflection temperature of above about 65° C. at 264 pounds per square inch.

* * * * *